(12) United States Patent
Sugioka

(10) Patent No.: US 9,228,676 B2
(45) Date of Patent: Jan. 5, 2016

(54) ELECTROOSMOTIC MOVABLE DEVICE

(71) Applicant: CANON KABUSHIKI KAISHA, Tokyo (JP)

(72) Inventor: Hideyuki Sugioka, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/223,536

(22) Filed: Mar. 24, 2014

(65) Prior Publication Data

US 2014/0202865 A1     Jul. 24, 2014

Related U.S. Application Data

(63) Continuation of application No. 12/842,875, filed on Jul. 23, 2010, now Pat. No. 8,715,479.

(30) Foreign Application Priority Data

Jul. 28, 2009    (JP) ................................ 2009-175779

(51) Int. Cl.

| | |
|---|---|
| *G01N 27/447* | (2006.01) |
| *F16K 99/00* | (2006.01) |
| *B01F 7/00* | (2006.01) |
| *B01F 13/00* | (2006.01) |
| *B01F 15/00* | (2006.01) |
| *B01L 3/00* | (2006.01) |

(52) U.S. Cl.
CPC ......... *F16K 99/0042* (2013.01); *B01F 7/00908* (2013.01); *B01F 13/0059* (2013.01); *B01F 15/00487* (2013.01); *F16K 99/0001* (2013.01); *F16K 99/0005* (2013.01); *F16K 99/0013* (2013.01); *F16K 99/0051* (2013.01); *F16K 99/0053* (2013.01); *B01F 13/0076* (2013.01); *B01L 3/50273* (2013.01); *B01L 3/502738* (2013.01); *F16K 2099/0094* (2013.01); *G01N 27/44752* (2013.01)

(58) Field of Classification Search
CPC . F16K 31/02; F16K 99/0001; F16K 99/0017; F16K 99/0021; F16K 99/0042; F16K 99/0051; G01N 27/44747; G01N 27/44752
See application file for complete search history.

(56) References Cited

U.S. PATENT DOCUMENTS

| | | | |
|---|---|---|---|
| 6,964,736 B2 * | 11/2005 | Quake et al. .................. 204/452 |
| 8,715,479 B2 * | 5/2014 | Sugioka ........................ 204/600 |

* cited by examiner

*Primary Examiner* — Alexander Noguerola
(74) *Attorney, Agent, or Firm* — Canon U.S.A., Inc., IP Division

(57) ABSTRACT

An electroosmotic movable device is provided, which includes a liquid chamber that houses a liquid, a conductive movable structure that is placed in the liquid chamber and has a rotating shaft or a supporting point and further has a conductive portion, and an electrode for applying an electric field to the conductive movable structure. The conductive movable structure is enabled to move by an electroosmotic flow which occurs in an electric double layer portion formed by being paired with an electric charge induced in the conductive movable structure owing to the electric field which is applied from the electrode.

5 Claims, 8 Drawing Sheets t = 0 ms t = 122 ms t = 244 ms t = 0 ms t = 20 ms t = 40 ms

ELECTROOSMOTIC MOVABLE DEVICE

CROSS-REFERENCE TO RELATED APPLICATIONS

This application is a continuation of U.S. patent application Ser. No. 12/842,875 filed Jul. 23, 2010, which claims the benefit of Japanese Patent Application No. 2009-175779, filed Jul. 28, 2009, all of which are hereby incorporated by reference herein in their entirety.

BACKGROUND OF THE INVENTION

1. Field of the Invention

The present invention relates to an electroosmotic movable device using induced-charge electro-osmosis, and more concretely relates to an electroosmotic movable device applicable to an actuator, a fluid valve, an optical scanner and the like.

2. Description of the Related Art

Micro-pumps using electro-osmosis are relatively simple in structure. They are used in the field of μTAS (Micro-Total Analysis System) and the like for the reason of being relatively simple in structure and being easily mounted into micro-channels.

Among them, micro-pumps using induced-charge electro-osmosis (ICEO: Induced-Charge Electro-osmosis) have attracted attention in recent years. The reasons of this include the fact that the micro-pumps can increase the flow velocity of liquids and can suppress chemical reactions occurring between the electrodes and the liquids by being capable of AC drive.

U.S. Pat. No. 7,081,189 and M. Z. Bazant and T. M. Squires, Phys. Rev. Lett. 92, 066101 (2004) disclose pumps using induced-charge electro-osmosis and having the following (1) and (2).

Specifically, (1) a pump (half coat type ICEO pump) which controls the flow of a liquid in such a manner that a coating of a dielectric thin film is applied to half of a metal post placed between electrodes to control the region of the electric charges induced in the metal post by an electric field applied. (2) A pump (asymmetrical metal post shape type ICEO pump) which controls the flow of a liquid in a constant direction by disposing a metal post in asymmetrical shape such as a triangle between electrodes.

K. A. Rose et al., Phys. Rev. E75, 011503 (2007) discloses rotation of a micro-rod using ICEP (Induced-Charge Electrophoresis).

Further, S. Gangwal, O. J. Cayre, M. Z. Bazant, and O. D. Velev, Phys. Rev. Lett. 100 058302 (2008) discloses the electrophoresis phenomenon of metal particles with an insulating coat applied to a half of the metal particles.

Meanwhile, a number of compact actuators (electrostatic actuators) using electrostatic force in the air are disclosed.

However, when an electrostatic actuator which is devised to be mainly used in the air is placed in an electrolytic solution such as water, the electric field is shielded by ions in the electrolytic solution, and therefore, the problem arises that the electrostatic force does not work. Thus, realization of a compact actuator has been difficult.

Further, in the art of moving a movable part in a solution by using external force such as magnetic force, not only reduction in size of the drive part has been difficult, but also drive of the movable part at a high velocity has been difficult due to frictional force or viscous resistance (flow resistance) which occurs on the interface of the solid and liquid due to the viscosity of the liquid.

Further, the arts described in U.S. Pat. No. 7,081,189, M. Z. Bazant and T. M. Squires, Phys. Rev. Lett. 92, 066101 (2004), K. A. Rose et al., Phys. Rev. E75, 011503 (2007) and S. Gangwal, O. J. Cayre, M. Z. Bazant, and O. D. Velev, Phys. Rev. Lett. 100 058302 (2008) do not suggest or disclose a so-called actuator technique that drives a movable body having a rotating shaft or a supporting point.

The present invention is made in view of such a background art, and provides an electroosmotic movable device which uses induced-charge electro-osmosis and can be used as an actuator or the like in a liquid, particularly in an electrolytic solution.

SUMMARY OF THE INVENTION

An electroosmotic movable device provided by the present invention includes a liquid chamber that houses a liquid, a conductive movable structure that is placed in the liquid chamber, and has one of a rotating shaft and a supporting point and has a conductive portion, and an electrode for applying an electric field to the conductive movable structure, wherein the conductive movable structure is enabled to move by an electroosmotic flow which occurs in an electric double layer portion formed by being paired with electric charges induced in the conductive movable structure owing to the electric field applied from the electrode.

According to the present invention, the electroosmotic movable device can be provided which uses induced-charge electro-osmosis and can be used as an actuator or the like in a liquid.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

An electroosmotic movable device according to the present invention includes a liquid chamber that houses a liquid, a conductive movable structure that is placed in the liquid chamber, and has one of a rotating shaft and a supporting point and has a conductive portion, and an electrode that applies an electric field to the conductive movable structure, wherein the conductive movable structure is enabled to move by an electroosmotic flow which occurs in an electric double layer portion formed by being paired with electric charges induced in the conductive movable structure owing to the electric field applied from the electrode.

The electroosmotic movable device according to the present invention can be used as an actuator in a liquid, for example, water by making use of an electroosmotic flow which occurs to an electric double layer portion formed by being paired with an electric charge induced to the conductive movable structure by the electric field applied from the electrode.

The conductive movable structure preferably includes a solid structure or an elastic structure having a conductive portion.

The electroosmotic movable device preferably has a unit for suppressing frictional force (solid-solid interface contact friction) between the conductive movable structure and a wall of the liquid chamber.

The electrode preferably includes a plurality of electrodes which gives electric fields in a plurality of directions to the conductive movable structure, and the conductive movable structure can preferably be driven while a direction of an electric field applied from the electrode is temporally switched.

Preferably, the liquid chamber is provided in one portion of a channel in which a liquid flows, the conductive movable structure placed in the liquid chamber is enabled to move by applying an electric field to the conductive movable structure to control a flow of the liquid in the channel. The electroosmotic movable device is preferably an actuator.

Preferably, the conductive movable structure has a mirror surface and the conductive movable structure is enabled to move by applying an electric field to the conductive movable structure to scan light incident on the mirror surface.

Embodiment 1

Figure 1:
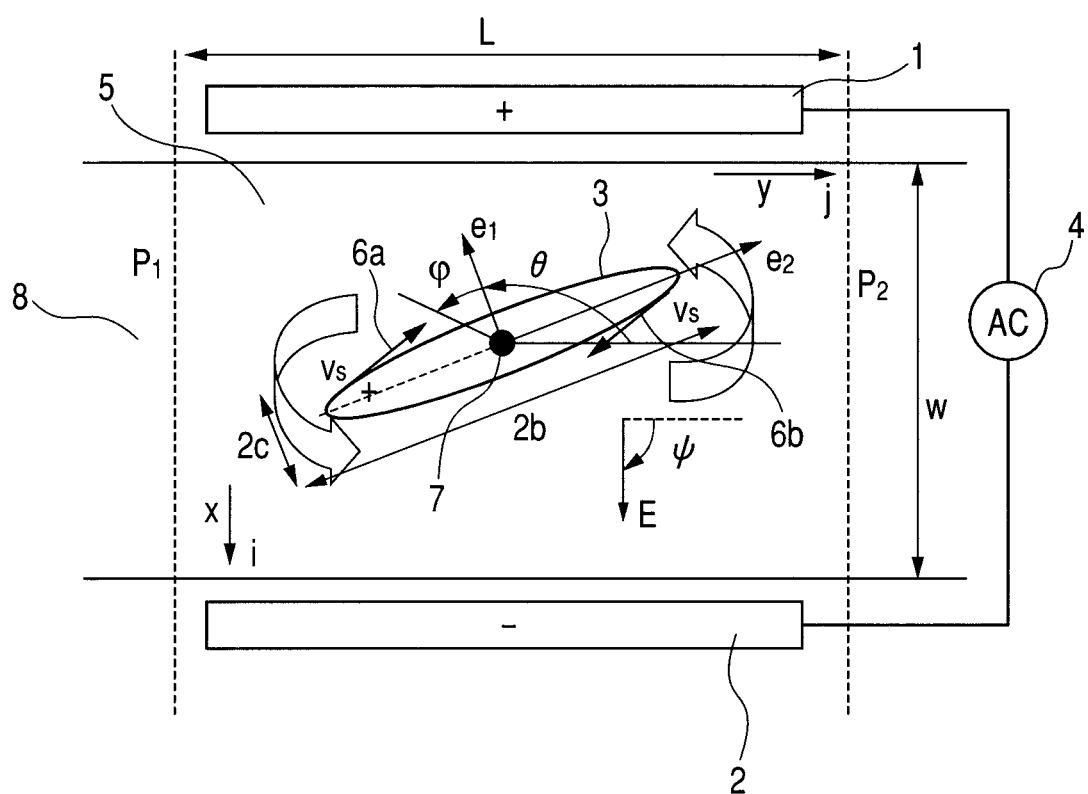
FIG. 1 is a sectional view illustrating one embodiment of an electroosmotic movable device of the present invention.

FIG. 1 is a sectional view illustrating one embodiment of an electroosmotic movable device of the present invention.

FIG. 1 illustrates a pair of electrodes 1 and 2, a conductive movable structure 3 having a rotating shaft or a supporting point and has a conductive portion, a power supply 4 and a liquid chamber 5, which is also used as a channel for a liquid, with a width w (for example, 100 μm), a length L (for example, 225 μm), and a depth d2 (>w), and the liquid chamber is filled with a polarizable liquid such as water and an electrolytic solution. Here, a pair of electrodes 1 and 2 is electrodes which apply an electric field to the conductive movable structure 3, and apply a DC or AC electric field to a channel 8. Further, electroosmotic flows 6a and 6b occur around the conductive movable structure 3 by an induced-charge electro-osmosis phenomenon when the electric field is applied, and the conductive movable structure 3 has a rotating shaft or a supporting point 7.

The conductive movable structure 3 has the rotating shaft or the supporting point 7, and has a conductive portion. The conductive movable structure 3 is made of a solid structure or an elastic structure. The concrete examples of the solid structure include a thick film of gold or platinum and carbon. The concrete examples of the elastic structure include a thin film of gold or platinum. Here, the conductive portion of the conductive movable structure 3 corresponds to the conductive movable structure, but the conductor movable structure may include a part other than the conductive portion.

The present invention includes the liquid chamber 5, the conductive movable structure 3 disposed in the liquid chamber 5, and the electrodes 1 and 2 which give the electric field to the conductive movable structure 3. By the electric field applied from the electrodes, electric charges are induced in the conductive portion of the conductive movable structure 3. The conductive movable structure 3 is enabled to move by the electroosmotic flows 6a and 6b which occur in the electric double layer portion formed in the interface of the conductor and the electrolytic solution by being paired with the electric charges. By the operation of the conductive movable structure, the electroosmotic movable device of the present invention can be used as an actuator in water.

In the present embodiment 1, the conductive movable structure 3 shows a conductive elliptic cylinder having the rotating shaft 7. In FIG. 1, the elliptic cylinder has a length $2b$ of a long axis and a length $2c$ of a short axis, a parameter $\phi$ expresses a position on the ellipse, and an angle $\theta$ is formed by an ellipse short axis main axis vector $e_1$ and a y-direction, and represents a rotational angle of the conductive elliptic cylinder.

FIG. 1 illustrates a slip velocity Vs, a channel inlet portion (channel left end) pressure $P_1$, a channel outlet portion (channel right end) $P_2$, x-direction unit vector i, a y-direction unit vector j, an electric field vector E, and an angle $\Psi$ formed by a y-axis and the electric field vector.

Figure 2A:
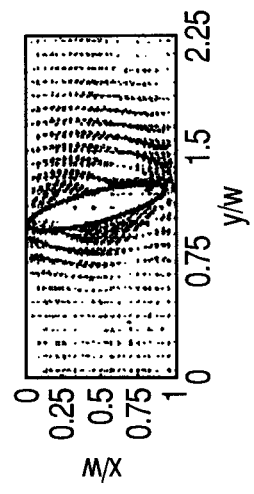
FIGS. 2A, 2B, 2C and 2D are diagrams illustrating one example of an effect obtained by driving the electroosmotic movable device of the present invention.
Figure 2B:
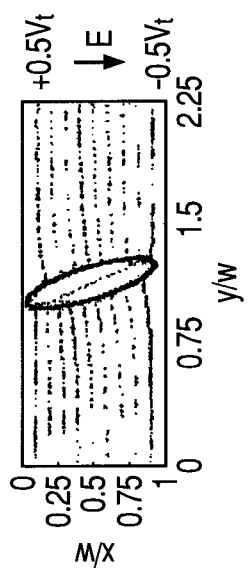
Figure 2C:
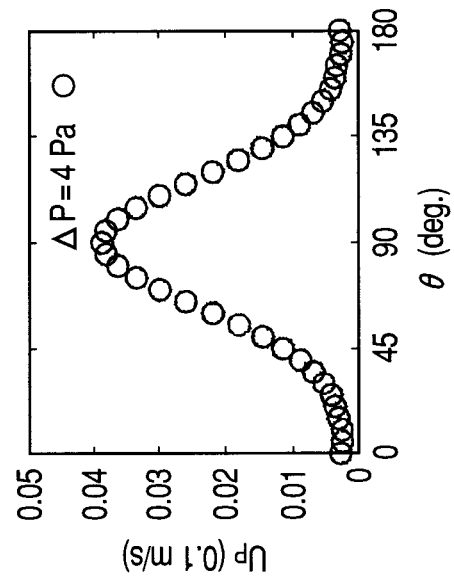
Figure 2D:
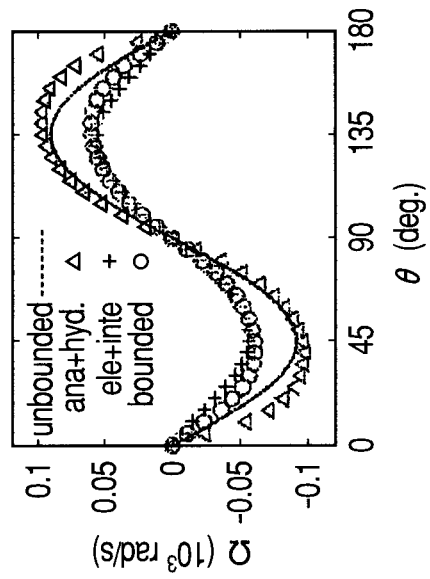

FIGS. 2A, 2B, 2C and 2D are diagrams illustrating one example of an effect obtained by driving the electroosmotic movable device of the present invention. FIGS. 2A, 2B, 2C and 2D illustrate nomograms of the electroosmotic movable device. FIG. 2A is a diagram illustrating a potential distribution in the channel when a voltage is applied to the electrodes 1 and 2. FIG. 2B is a diagram of a flow velocity vector distribution in the channel. FIG. 2C is a diagram illustrating rotational angle $\theta$-dependence of an angular velocity Q of rotation of the conductive elliptic cylinder. FIG. 2D is a diagram illustrating the rotational angle $\theta$-dependence of an average flow velocity Up measured at the inlet of the liquid chamber 5.

The calculated values are calculated by a coupled calculation method which alternately repeats a Stokes fluid equation considering an induced-charge electro-osmosis effect and a Laplace equation which finds an electrostatic field. Calculation is made with the position of the rotating shaft 7 set as (x/w, y/w)=(0.47, 1.125), w=100 μm, L/w=2.25, b/c=4.6, c/w=0.1, and an applied voltage $V_0$=1.19 V. Note that a pressure difference $\Delta P$ is set as 4 Pa in FIG. 2D. In FIG. 2C, circle marks represent calculation results with the highest precision by the above described calculation method, and the other marks represent results by the other approximate calculation methods. FIGS. 2A to 2D illustrate that when a DC or AC voltage of about 1 V is applied, the device has a high angular velocity of about 50 rad/s at the maximum in water and can control the average flow velocity.

Figure 3A:
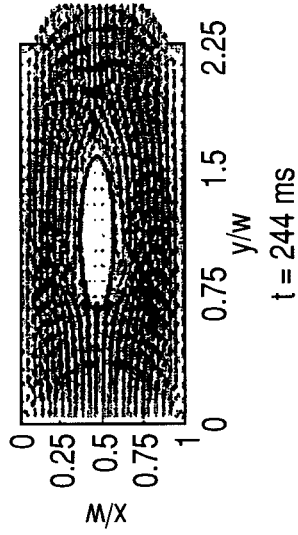
FIGS. 3A, 3B, 3C, 3D, 3E and 3F are diagrams illustrating one example of an operation of driving the electroosmotic movable device of the present invention.
Figure 3B:
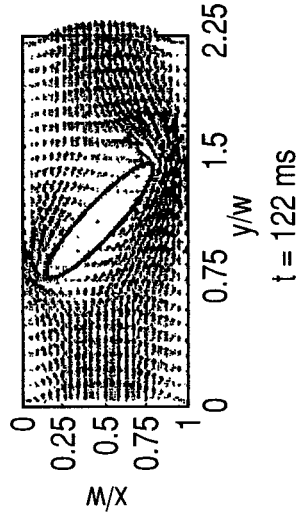
Figure 3C:
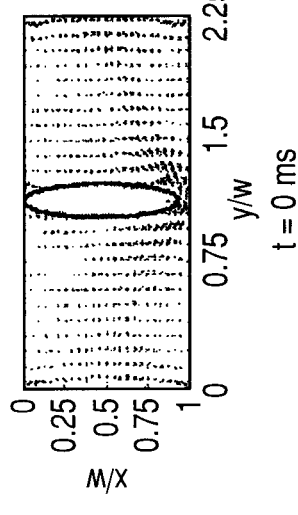
Figure 3D:
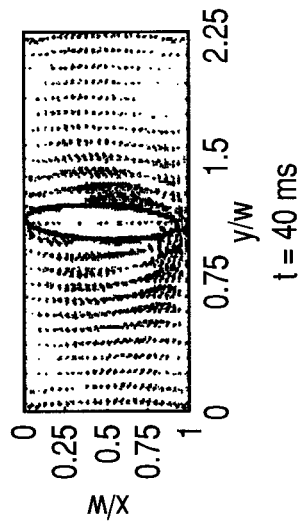
Figure 3E:
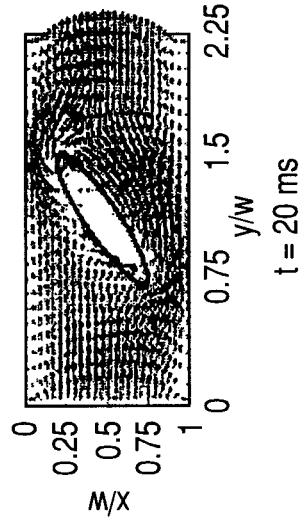
Figure 3F:
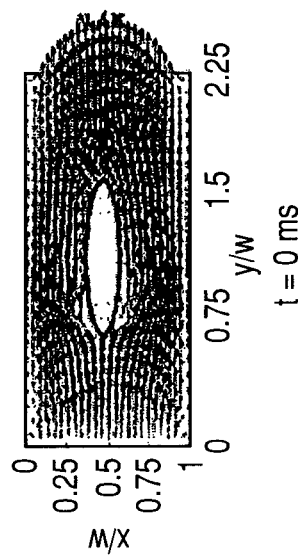

FIGS. 3A, 3B, 3C, 3D, 3E and 3F are diagrams illustrating one example of the operation of driving the electroosmotic movable device of the present invention. FIGS. 3A, 3B and 3C show results of calculating the opening operation of the conductive movable structure 3 as a valve with the valve in a closed state and the applied voltage turned off. Here, the rotation failure in the initial operation is prevented by shifting the position of the rotating shaft 7 from the center of the channel as (x/w, y/w)=(0.47, 1.125). Further, FIGS. 3D, 3E and 3F show results of calculating the closing operation of the conductive movable structure 3 as a valve with the valve in an open state and a voltage of 1.19 V being applied. FIGS. 3A to 3F illustrate that the high-velocity fluid valve using ICEP (Induced-Charge Electrophoresis) can be realized, which is brought into an open state at about 244 ms and can be brought into a closed state at about 40 ms.

Figure 4A:
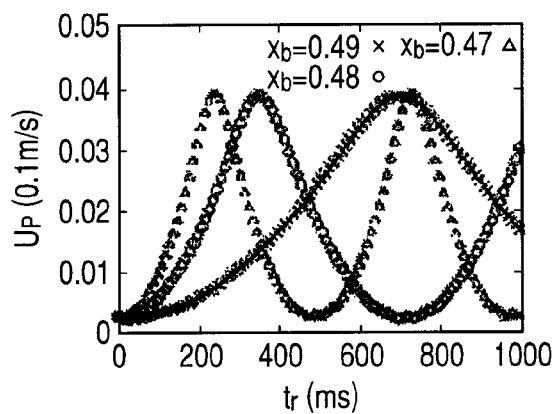
FIGS. 4A, 4B, 4C, 4D, 4E and 4F are diagrams illustrating one example of the operation of driving the electroosmotic movable device of the present invention.
Figure 4D:
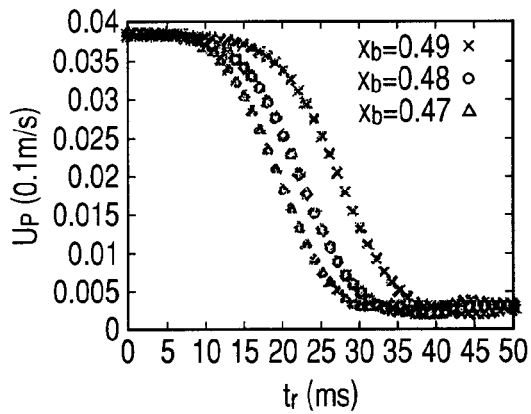
Figure 4B:
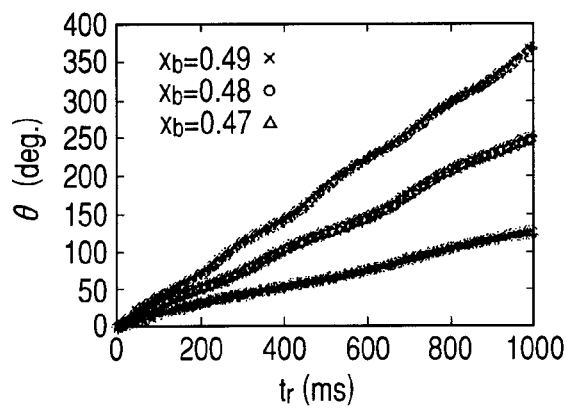
Figure 4E:
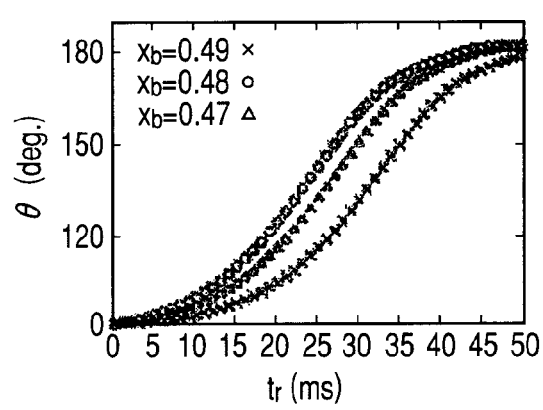
Figure 4C:
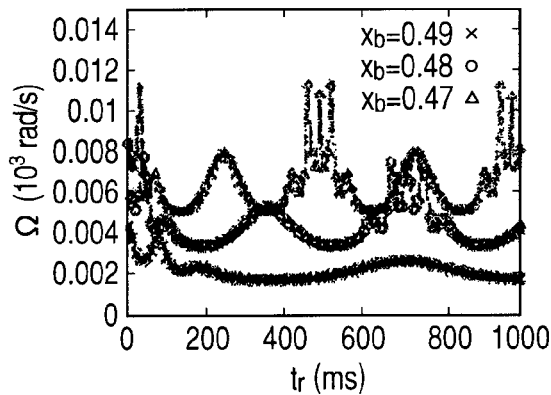
Figure 4F:
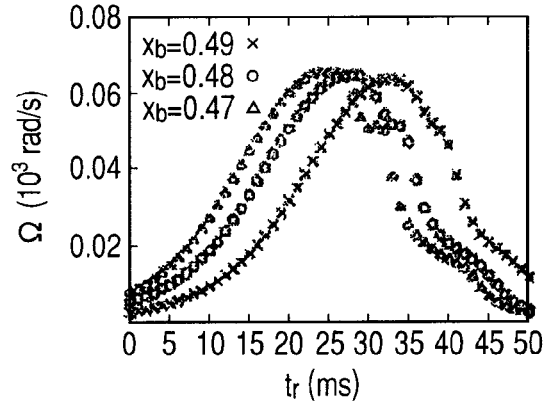

FIGS. 4A, 4B, 4C, 4D, 4E and 4F are diagrams illustrating one example of the operation of driving the electroosmotic movable device of the present invention. FIGS. 4A to 4F illustrate the time-series development of an average flow velocity Up, the rotational angle θ and the angular acceleration Ω at the time of an opening operation (FIGS. 4A, 4B and 4C) and at the time of a closing operation (FIGS. 4D, 4E and 4F) when the x position of the rotating shaft was x/w=0.47, 0.48 and 0.49. FIGS. 4A, 4B and 4C illustrate that in the state in which the voltage is in an off state, the valve which is the conductive movable structure 3 continues to rotate and causes pulsating flow. Further, the time of opening tends to be shorter, as the shift amount of the rotating shaft position from the center is larger. In contrast with this, the time of closing tends to be longer as the shift amount of the rotating shaft position from the center is larger.

Figure 5A:
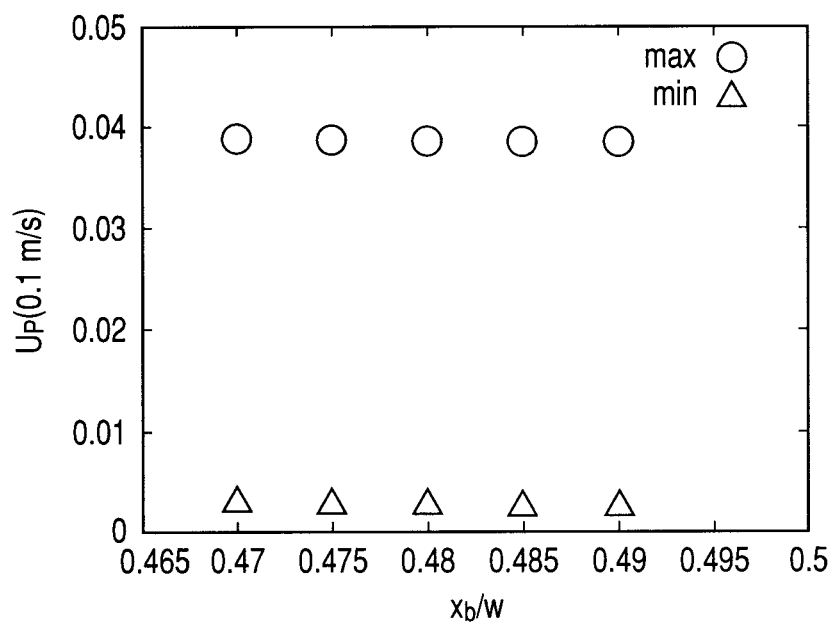
FIGS. 5A and 5B are diagrams illustrating one example of the operation of driving the electroosmotic movable device of the present invention.
Figure 5B:
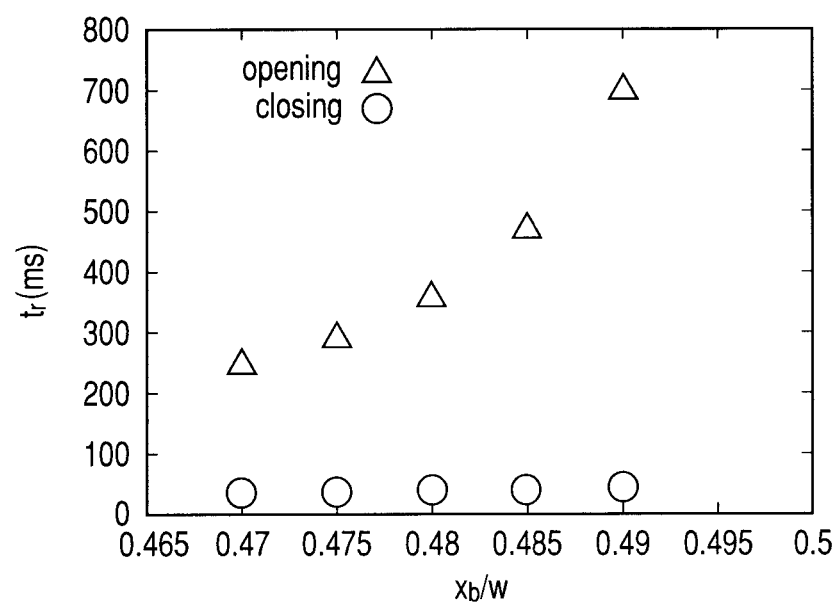

FIGS. 5A and 5B are diagrams illustrating one example of the operation of driving the electroosmotic movable device of the present invention. FIG. 5A is a nomogram illustrating the relation of a response time tr and the average flow velocity Up with respect to the rotating shaft position xb/w. FIG. 5B illustrates that when the rotating shaft is made close to the center, the response time tr abruptly becomes long, and therefore, large shift of the shaft can be preferably performed so long as the conductive elliptic cylinder does not contact the channel wall.

Figure 6:
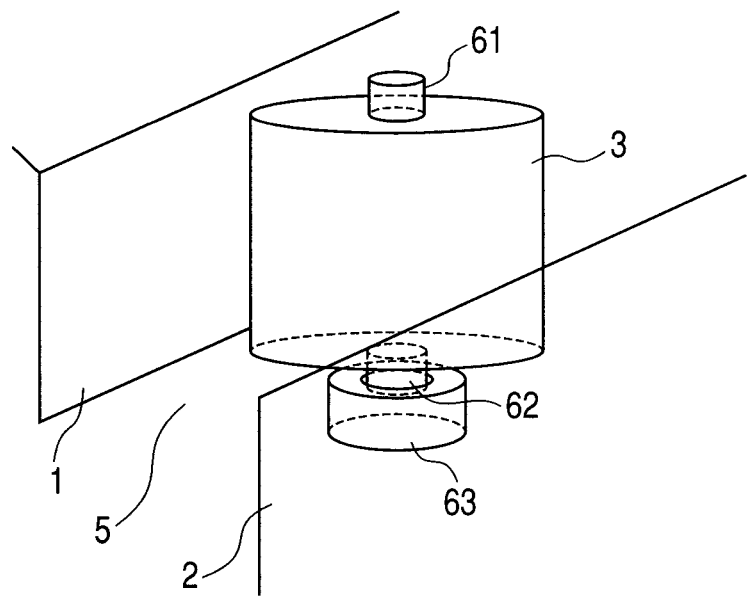
FIG. 6 is a schematic view illustrating one example of a rotating shaft of a conductive movable structure used in the present invention.

FIG. 6 is a schematic diagram showing one example of the rotating shaft of the conductive movable structure of the electroosmotic movable device of the present invention. FIG. 6 illustrates a concrete structure concerning the rotating shaft. Rotating shaft rods 61 and 62 are those of the rotating shaft 7, and are connected to the conductive movable structure 3. A bearing 63 is a bearing for the rotating shaft rod 62 with a hollow cylinder structure. The bearing 63 having a hollow circular cylinder structure has an outside diameter smaller than the length 2b of the conductive movable structure 3, and therefore, reduces the frictional force by decreasing the contact area between the conductive movable structure 3 and the channel wall to enable the conductive movable structure 3 to move easily. More specifically, the rotating shaft rod 62 and the bearing 63 are units which suppress the frictional force (contact friction between a solid and a solid) between the conductive movable structure and the liquid chamber wall, and have the effect of easily enabling the conductive movable structure 3 to move.

The present invention brings about an effect of providing an electroosmotic movable device which can be used as an actuator in an electrolyte which can be enabled to move in the state in which the electric charges of the movable body are electrostatically shielded by ions in the electrolyte by enabling the conductive movable structure to move by use of an electroosmotic flow which occurs in an electric double layer portion induced in the conductive movable structure owing to the electric field applied to the conductive movable structure. More specifically, the present invention provides the effect of providing a new compact actuator which solves the problem of the electrostatic shield which arises when the electrostatic actuator is disposed in the electrolyte.

Further, in the art of moving a movable part in a solution by using an external force such as magnetic force, not only reduction in size of the drive part is difficult, but also driving the movable part at a high velocity is difficult due to the frictional force or viscous resistance which occurs to the interface between the solid and the liquid due to viscosity of the liquid. However, in the present invention, the movable part is driven to slide in the fluid by using the electroosmotic flow on the interface between the solid and liquid, and therefore, the present invention provides the effect of significantly avoiding the problem of the flow resistance due to viscosity of the liquid.

Embodiment 2

Figure 7A:
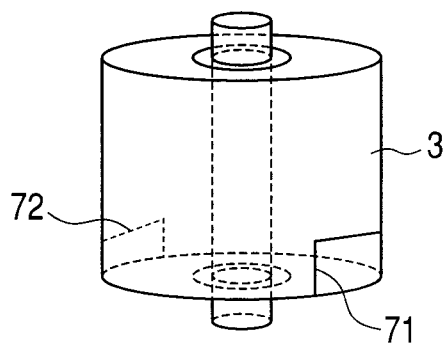
FIGS. 7A and 7B are schematic views illustrating another example of the conductive movable structure used in the present invention.
Figure 7B:
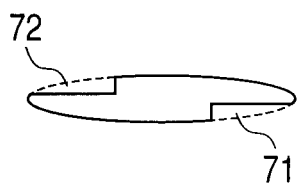
Figure 8:
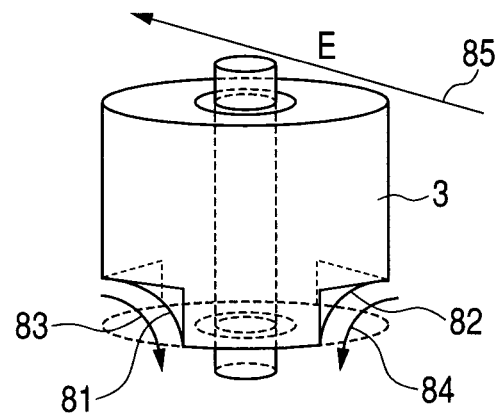
FIG. 8 is a schematic view illustrating another example of the conductive movable structure used in the present invention.

Embodiment 2 is the same as embodiment 1 except that the frictional force suppressing unit is constituted of a conductive movable structure having a floating structure. FIGS. 7A, 7B and 8 are schematic views illustrating other examples of the conductive movable structure used in the electroosmotic movable device of the present invention. The conductive movable structure of FIG. 7A has a propeller structure including notched structures 71 and 72 at a bottom portion of the conductive movable structure. The propeller structure provides the effect of giving a buoyancy force to the conductive movable structure 3, reducing the friction and enabling the conductive movable structure 3 to move at a high velocity owing to the hydrodynamic interaction between the fluid and the propeller structure at the time of rotation.

Further, the conductive movable structure of FIG. 8 is provided with slopes 81 and 82 having inclination angles with respect to the channel bottom surface at the bottom portion of the conductive movable structure. The slopes provide the effect of reducing contact friction between the conductive movable body 3 and the channel wall and enabling high-velocity movement by generating induced-charge electroosmotic flows 83 and 84 going to the channel bottom surface from the conductive movable structure 3 when an electric field 85 is applied, and causing the conductive movable structure 3 to generate a buoyancy.

Embodiment 3

Embodiment 3 provides an electroosmotic movable device that has an electrode including a plurality of electrodes which gives electric fields in a plurality of directions to a conductive movable structure and drives the conductive movable structure while temporally switching the direction of the electric field applied from the electrode.

Figure 9:
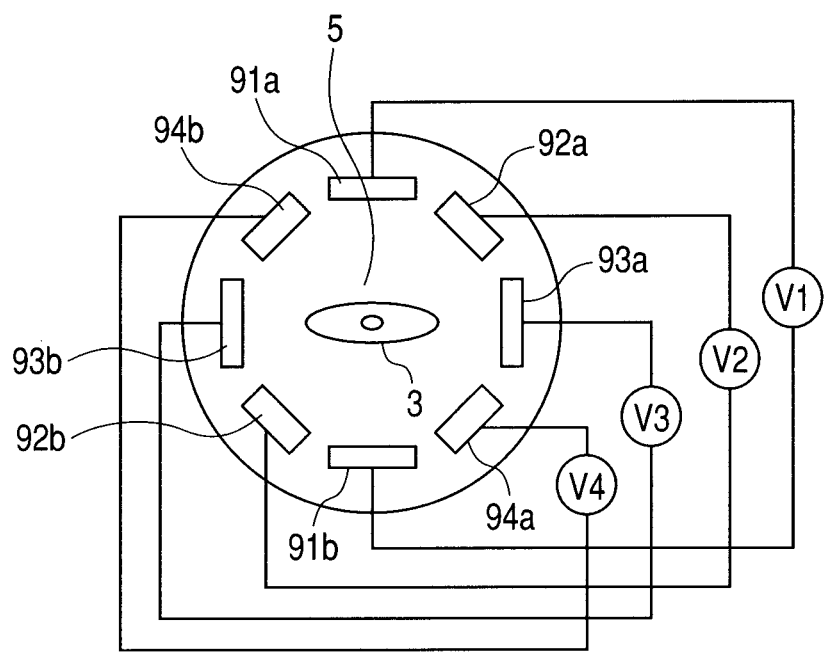
FIG. 9 is a schematic view illustrating another embodiment of the electroosmotic movable device of the present invention.

FIG. 9 is a schematic view illustrating another embodiment of the electroosmotic movable device of the present invention. Embodiment 3 is the same as embodiment 1 except that embodiment 3 has, in the liquid chamber 5, electrodes 91a and 91b, 92a and 92b, 93a and 93b, and 94a and 94b which give electric fields in a plurality of directions to the conductive movable structure, and drives the conductive movable structure by temporally switching the electric field direction. Embodiment 3 particularly includes the electrodes 91a and 91b, 92a and 92b, 93a and 93b, and 94a and 94b which give electric fields in four directions. Embodiment 3 provides the effect of being capable of rotating the conductive elliptic cylinder of the conductive movable structure at a high velocity by driving the conductive movable structure so that the electric field direction temporally rotates by applying the electric field with shifting the phases of the voltages of the power supplies V1 to V4.

Embodiment 4

Embodiment 4 provides an electroosmotic movable device in which the conductive movable structure has a mirror surface, and the conductive movable structure is enabled to move by applying an electric field to the conductive movable structure to scan light which is incident on the mirror surface.

Figure 10:
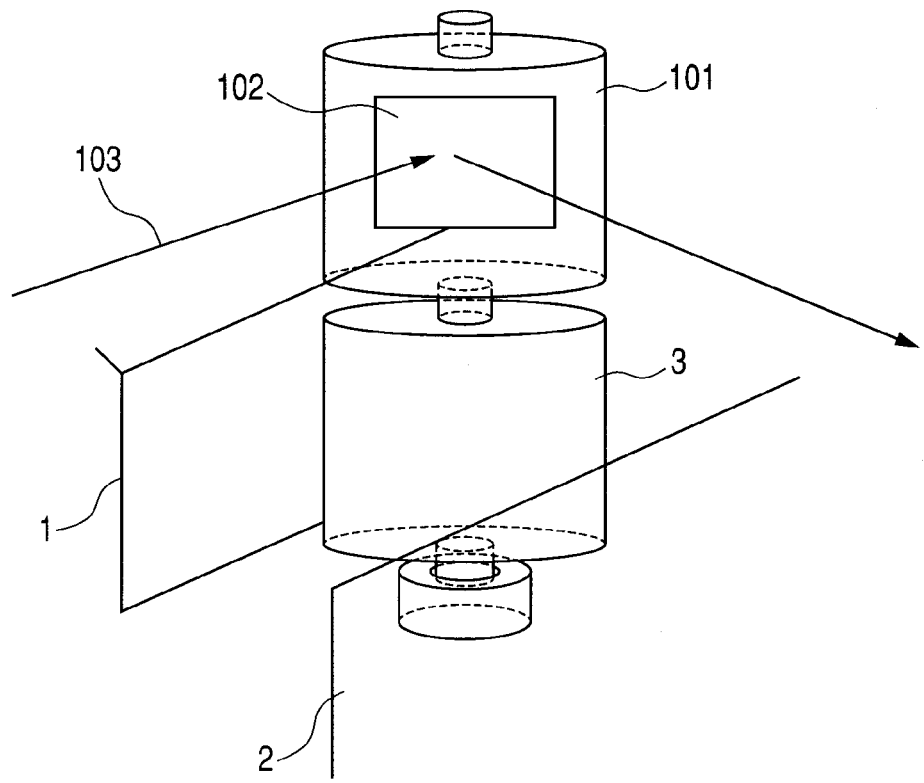
FIG. 10 is a schematic view illustrating another embodiment of the electroosmotic movable device of the present invention.

FIG. 10 is a schematic view illustrating another embodiment of the electroosmotic movable device of the present invention. Embodiment 4 is the same as embodiment 1 except that an optical structure 101 connected to the conductive movable structure 3 has a mirror surface 102, the rotational operation of the conductive movable structure 3 and the optical structure 101 is performed by applying an electric field, and a light 103 incident on the mirror surface is scanned. Use of the electroosmotic movable device provides the effect of scanning light at high velocity with a simple structure.

Embodiment 5

Figure 11:
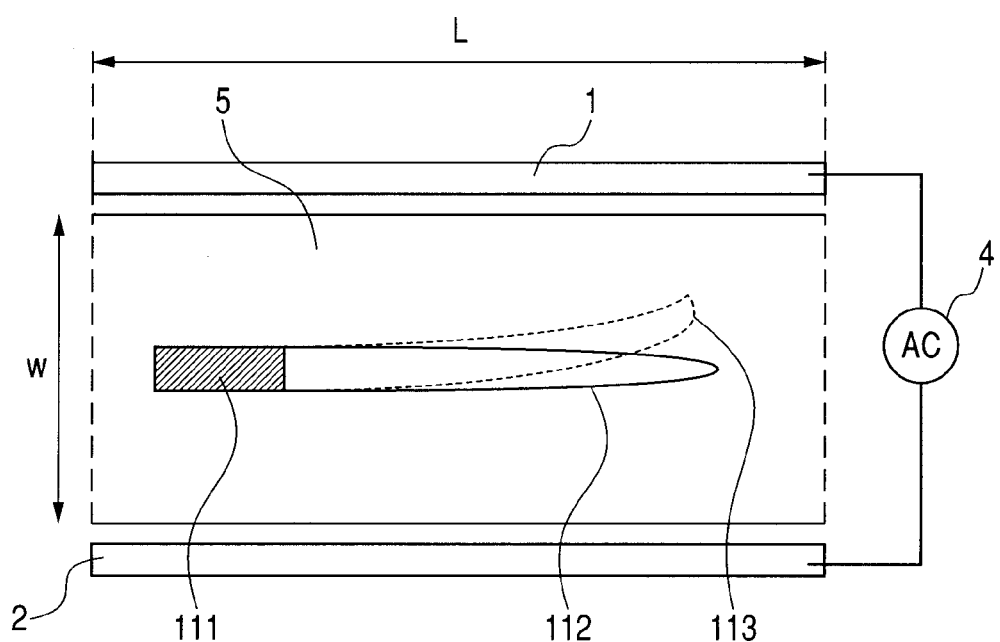
FIG. 11 is a schematic view illustrating another embodiment of the electroosmotic movable device of the present invention.

Embodiment 5 provides an electroosmotic movable device in which the conductive movable structure is constituted of a conductive beam having an elasticity which is connected to a supporting part fixed in the liquid chamber, and an electric field is applied to the conductive movable structure to deform the beam part, thereby controlling the flow amount. FIG. 11 is a schematic view illustrating this electroosmotic movable device.

In the device shown in FIG. 11, the conductive movable structure is constituted of a conductive beam 112 having an elasticity connected to a supporting part 111 and having an elliptically-shaped tip portion.

Embodiment 5 is the same as embodiment 1 except that, by applying an electric field, the beam 112 is given a rotary torque along the electric field, thereby causing the beam to warp in the direction of the electric field as shown by numeral 113, actively controlling the flow amount in the channel. Use of the electroosmotic movable device provides the effect of finely controlling the flow amount in a micro-channel with a simple structure.

The electroosmotic movable device of the present invention can be used as an actuator or the like in a liquid, particularly in an electrolytic solution using induced-charge electroosmosis.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An electroosmotic movable valve comprising:
a channel in which a liquid flows;
a conductive movable structure that is placed in the channel, and has a rotating shaft, such that the placed position of the shaft is shifted from the center of the channel to a width direction of the channel; and
an electrode configured to apply an electric field to the conductive movable structure,
wherein the conductive movable structure is enabled to rotate based on the rotating shaft to regulate the liquid flow by an electroosmotic flow which occurs in an electric double layer portion formed by being paired with electric charges induced in the conductive movable structure owing to the electric field applied from the electrode.

2. An electroosmotic movable valve according to claim 1, wherein the conductive movable structure in an open state moves into a closed state of the channel by applying the electric field from the electrode.

3. An electroosmotic movable valve according to claim 1, wherein the conductive movable structure in a closed state moves into an open state of the channel owing to the liquid flow by turning off the electric field from the electrode.

4. An electroosmotic movable valve according to claim 1, wherein the conductive movable structure has an elliptic shape having a long axis and a short axis.

5. An electroosmotic movable valve according to claim 1, wherein the shaft is placed at position of (x/w) ranged from (0.47) to (0.49), wherein w denotes a width of the channel and x denotes a located distance of the shaft in a width direction of the channel.

* * * * *